United States Patent
Esser et al.

(10) Patent No.: US 6,703,409 B2
(45) Date of Patent: Mar. 9, 2004

(54) 2'-HALO-3',5'-DIALKOXYPHEN-1'-YL-IMINO-2-IMIDAZOLIDINE AND THE USE THEREOF AS A DRUG

(75) Inventors: Franz Esser, Ingelheim (DE); Pascale Pouzet, Biberach (DE); Naoki Ishiguro, Osaka (JP); Hisato Kitagawa, Osaka (JP); Ikunobu Muramatsu, Fukui (JP)

(73) Assignee: Boehringer Ingelheim Pharma GmbH & Co KG, Ingelheim (DE)

( * ) Notice: Subject to any disclaimer, the term of this patent is extended or adjusted under 35 U.S.C. 154(b) by 18 days.

(21) Appl. No.: 10/351,486

(22) Filed: Jan. 24, 2003

(65) Prior Publication Data

US 2003/0162822 A1 Aug. 28, 2003

Related U.S. Application Data

(60) Provisional application No. 60/354,465, filed on Feb. 5, 2002.

(30) Foreign Application Priority Data

Jan. 31, 2002 (EP) .............................................. 02002352

(51) Int. Cl.$^7$ .................. A61K 31/4168; C07D 233/50
(52) U.S. Cl. .................................... 514/392; 548/333.1
(58) Field of Search ........................ 548/333.1; 514/392

(56) References Cited

U.S. PATENT DOCUMENTS 4,244,957 A    1/1981 Ramuz
4,262,005 A *  4/1981 McCarthy et al. .......... 514/392

FOREIGN PATENT DOCUMENTS

| DE | 22 20 906 A | 11/1973 |
|---|---|---|
| DE | 25 21 709 A | 2/1976 |
| EP | 0 202 461 A1 | 11/1986 |
| EP | 0 887 346 A2 | 12/1998 |
| EP | 0 902 218 A1 | 3/1999 |
| FR | 2208671 A | 6/1974 |
| WO | wo 96/32939 A1 | 10/1996 |

OTHER PUBLICATIONS

Abstract for EP 0 202 461, 1986.
Abstract for EP 0 887 346, 1998.
Abstract for EP 0 902 218, 1999.
Chemical Abstract: 81:63628 CA for FR 2,208,671 A1, 1974.
Chemical Abstract: 84:180214 CA for DE 2 521 709 A1, 1976.
Chemical Abstract: 80:37152 CA for DE 2 220 906 A1, 1974.

* cited by examiner

*Primary Examiner*—Laura L. Stockton
(74) *Attorney, Agent, or Firm*—Robert P. Raymond; Anthony P. Bottino; Timothy K. Witkowski

(57) ABSTRACT

The present invention relates to 2'-halo-3',5'-dialkoxyphen-1'-yl-imino-2-imidazolidine, the tautomeric 2'-halo-3',5'-dialkoxyanilino-2-imidazoline and/or the pharmacologically acceptable salts thereof and their use as pharmaceutical compositions.

20 Claims, No Drawings

2'-HALO-3',5'-DIALKOXYPHEN-1'-YL-IMINO-2-IMIDAZOLIDINE AND THE USE THEREOF AS A DRUG

APPLICATION DATA

This application claims benefit to U.S. provisional application Ser. No. 60/354,465 filed Feb. 5, 2002 and EP 02002352.9 filed Jan. 31, 2002.

TECHNICAL FIELD OF THE INVENTION

The present invention relates to 2'-halo-3',5'-dialkoxyphen-1'-yl-imino-2-imidazolidine, the tautomeric 2'-halo-3',5'-dialkoxyanilino-2-imidazolines and/or the pharmacologically acceptable salts thereof and their use as pharmaceutical compositions, particularly for treating urinary incontinence.

BACKGROUND

Numerous examples of the category of phenylimino-imidazoles and -imidazolidines are known. The best known is possibly clonidine, 2',6'-dichlorophen-1'-yl-imino-2-imidazolidine.

With regard to the compound according to the invention, the number of structurally similar examples known is limited by their nature.

DE 2220906 describes a category of phenylimino-imidazoles of therapeutic benefit to which the compound according to the invention are structurally related. The compounds according to the invention or their properties in relation to the treatment of urinary incontinence are not disclosed.

JP 48-76870 discloses a category of phenylimino-imidazoles to which the compound according to the invention are structurally related. The compounds described therein count as vasoconstrictors and hypotensive agents. Specifically, 2-(phenylamino)-2-imidazoline and clonidine are disclosed.

The compounds according to the invention or their properties in relation to the treatment of urinary incontinence are not disclosed.

WO 96/32939, to which reference is hereby expressly made in its entirety, discloses a category of phenylimino-imidazolidines for the treatment of urinary incontinence to which the compound according to the invention are structurally related. The compounds according to the invention are not disclosed.

EP0887346 discloses another class of phenylimino-imidazolidines, phenylmethylen-imidazolidines, phenyloxymethylen-imidazolidines in that the phenyle-group mandatorily is substituted by an ureido (RR'NCONR"—), an sulfamoylaminio-group (RR'NSO$_2$NR"—) or sulfonamido- (RR'NSO$_2$—)-group. Theses compounds shall have an alpha 1L agonistic effect.

U.S. Pat. No. 4,244,957 discloses phenyliminoimidazolidines which are substituted at one of imiazolidine-nitrogen atom for treating hypertension. The compounds of the present invention are not disclosed.

DE2521709 discloses phenyliminoimidazolidines which again are substituted at one of imiazolidine-nitrogen atom for treating hypotension. The compounds of the present invention are not disclosed.

EP0202461 discloses phenyliminoimidazolidines which are substituted at an imino-nitrogen atom for treating heart-diseases. The compounds of the present invention are not disclosed.

FR2208671 discloses phenyliminoimidazolidines which are substituted at the imino-nitrogen atom and/or an imiazolidine-nitrogen atom which shall have hypotensive, sedative, anagetic and antisecretoric effect. The compounds of the present invention are not disclosed.

For the sake of completeness a search report also made reference to EP0902218, which however does not deal with chemical compounds.

In the context of the present invention, by incontinence is meant the involuntary release of urine, i.e. weakness of the urethral contraction. The various forms of urinary incontinence include urge incontinence, reflex incontinence, overflow incontinence and stress or load incontinence. The most common forms of urinary incontinence include load incontinence or stress incontinence. These affect women in particular after more or less difficult childbirth. The reason for this is that pregnancy and childbirth can easily lead to weakening of the pelvic floor. Other causes of incontinence may be found, for example, in damage to the nerves of the pelvic floor, a congenitally short urinary tract or damage to the sphincter muscle.

SUMMARY OF THE INVENTION

It has now surprisingly been found that the compounds of formula I have an outstanding agonistic effect on alpha-1L-receptors. The substances have a highly selective effect on the urethra and prevents urinary incontinence.

One aspect of the present invention is therefore to develop a drug with which urinary incontinence can be treated better, i.e more selectively.

Another aspect of the invention consists in developing drugs which act on the contracting mechanisms of the urethra without seriously affecting other organs such as peripheral blood vessels.

Another objective is to develop a non-toxic drug with few side effects.

Overall, therefore, the aim of the present invention is to find an active substance with one or more of the abovementioned profiles and to develop a suitable medicament from it.

DETAILED DESCRIPTION OF THE INVENTION

The compounds according to the invention are represented by the following structure (formula I):

Formula I:

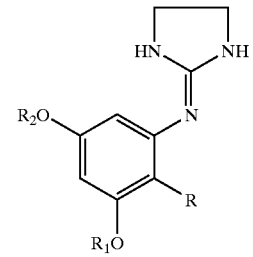

whereby

R stands for F, Cl, Br, CF$_3$, CH$_2$F or CHF$_2$,

R$_1$ and R$_2$ independently of each other may be any C$_1$ to C$_6$-alkyl, like methyl (Me), ethyl (Et), propyl (Pr), isopropyl (iPr), 1-butyl (Bu), 2-butyl (2-Bu), tert.butyl (tBu), pentyl (Pen), hexyl (Hex) etc.

Preferred are compounds with

R being F, Cl, Br or $CF_3$ and
$R_1$ and $R_2$ independently of each being an unbranched $C_1$ to $C_6$-alkyl.

More preferred are compounds with

R being Cl, Br or $CF_3$ and
$R_1$ and $R_2$ both being the same unbranched $C_1$ to $C_4$-alkyl.

Even more preferred are compounds with

R being Cl or Br and
$R_1$ and $R_2$ both being methyl, ethyl or propyl.

Most preferred are compounds with

R being Cl and
$R_1$ and $R_2$ both being methyl or ethyl.

In the context of the present invention these compounds represented by formula I are named as 2'-halo-3',5'-dialkoxyphen-1'-yl-imino-2-imidazolidine. In the context of the present invention the term "imidazolidine" stands for 4,5-dihydroimidazole, whereby one starts counting by one nitrogen atom and goes to the next nitrogen atom by passing the one-carbon-bridge. In case of any conflicts between a representation by a structure-formula or by a name, the representation by the structure formula shall prevail.

Likewise, the compounds may also be present in the tautomeric form according to Formula II:

Formula II:

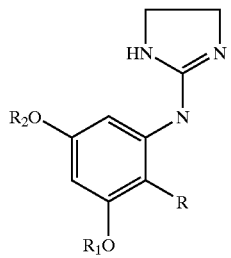

whereby the substituents R, $R_1$ and $R_2$, are as defined above.

In the context of the present invention these compounds represented by formula II are named as 2'-halo-3',5'-dialkoxyphen-1'-yl-amino-2-imidazolines (2'-halo-3',5'-dialkoxyanilino-2-imidazolines). In case of any conflicts between a representation by a structure-formula or by a name, the representation by the structure formula shall prevail.

Among these compounds the preferred compounds are

2'-chloro-3',5'-dimethoxyphen-1'-yl-imino-2-imidazolidine
  (based on formula I R=Cl, $R_1$=Me, $R_2$=Me),
2'-chloro-3',5'-diethoxyphen-1'-yl-imino-2-imidazolidine,
  (based on formula I R=Cl, $R_1$=Et, $R_2$=Et),
2'-chloro-3',5'-dipropyloxyphen-1'-yl-imino-2-imidazolidine, (based on formula I R=Cl, $R_1$=Pr, $R_2$=Pr),
2'-bromo-3',5'-dimethoxyphen-1'-yl-imino-2-imidazolidine,
  (based on formula I R=Br, $R_1$=Me, $R_2$=Me),
2'-bromo-3',5'-diethoxyphen-1'-yl-imino-2-imidazolidine,
  (based on formula I R=Br, $R_1$=Et, $R_2$=Et),
2'-bromo-3',5'-dipropyloxyphen-1'-yl-imino-2-imidazolidine, (based on formula I R=Br, $R_1$=Pr, $R_2$=Pr), the tautomeric forms of any of theses compounds according to formula II or pharmacologically acceptable salts of any of the two tautomeric forms of theses compounds.

Among these compounds are more preferred

2'-chloro-3',5'-dimethoxyphen-1'-yl-imino-2-imidazolidine,
  (based on formula I R=Cl, $R_1$=Me, $R_2$=Me),
2'-bromo-3',5'-dimethoxyphen-1'-yl-imino-2-imidazolidine,
  (based on formula I R=Br, $R_1$=Me, $R_2$=Me), the tautomeric forms of these compounds according to formula II or pharmacologically acceptable salts of any of the two tautomeric forms of these compounds.

Most preferred is

2'-chloro-3',5'-dimethoxyphen-1'-yl-imino-2-imidazolidine, its tautomeric form 2'-chloro-3',5'-dimethoxyanilino-2-imidazoline or a pharmacologically acceptable salts thereof.

The present description does not distinguish between the two described tautomeric structures according to formula I or II as they are considered to be equivalent. The present description also does not distinguish between the free base of the compounds and a pharmacologically acceptable acid addition salt thereof unless otherwise expressly stated. As a consequence thereof, if one of the compounds is disclosed by name of structure formula, the corresponding tautomeric form and pharmacologically acceptable salts of both tautomeric forms are meant as well unless otherwise expressly stated.

The substances may occur both as a free base or as an acid addition salt.

Examples of such salts are inorganic acids such as hydrochloric acid, hydrobromic acid, sulphuric acid, phosphoric acid or organic acids such as acetic acid, citric acid, tartaric acid, malic acid, succinic acid, fumaric acid, p-toluenesulphonic acid, benzenesulphonic acid, methanesulphonic acid, lactic acid, ascorbic acid and others.

Preferably, the compounds according to the invention are used in the form of the hydrochloric acid salt.

The compounds according to the invention may be administered as a medicament by oral route, by inhalation, intranasally, intravenously, by subcutaneous, intramuscular, transdermally, vaginally or as a suppository. Oral administration is preferred.

The compounds may be administered on their own or in conjunction with other suitable active substances.

To determine the optimum dose of the active substance for urinary incontinence, various framework conditions have to be taken into account such as, for example, the age and body weight of the patient, the nature and stage of the disease.

The preferred dose for humans is between 0.001 mg and 1 g per day, preferably between 0.001 mg and 100 mg, and is most preferably between 0.01 mg and 10 mg.

In some cases a smaller amount may be sufficient, whereas in other cases a larger total amount may be needed.

The total daily dose may be taken in one go or in several portions, depending on the therapeutic regimen. The therapeutic regimen may also prescribe intervals of more than one day between the doses.

The active substance according to the invention may be administered orally in various formulations, e.g. as a solid, in liquid form, as a powder, in the form of tablets, as a coated tablet, sugar-coated tablets, as an oral disintegrating tablet, as a sublingual tablet, in a capsule, in granulated form, as a suspension, solution, emulsion, elixir or syrup, in the form of drops or in other forms.

A powder may be prepared, for example, by grinding the particles of active substance to a suitable size.

Dilute powders may be prepared, for example, by finely grinding the powdered substance with a non-toxic carrier material such as lactose, for example, and producing it as a powder. Other carrier materials suitable for this purpose are other carbohydrates such as starch or mannitol. These powders may possibly contain flavourings, preservatives, dispersing agents, colourings and other pharmaceutical excipients.

Capsules may be produced, starting from a powder of the type mentioned above or other powders, which are placed into a capsule, preferably a gelatine capsule.

It is also possible to introduce lubricants known from the prior art into the capsule or to use them to seal the two halves of the capsule. The dissolution rate of a capsule can be increased by the addition of disintegrant or solubilising substances, such as, for example, carboxymethylcellulose, carboxymethylcellulose calcium, lowly-substituted hydroxypropylcellulose, calcium carbonate, sodium carbonate, sodium carboxymethyl starch, crospovidone, croscarmellose sodium and other substances. The dissolution rate of a capsule can be also controlled by processing the contents into granulated forms, pellets, or other forms, by addition of binders, dissolution-control agents, or other excipients. The active substance may be contained in the capsule not only as a solid but also in solution or in suspension, e.g. in vegetable oil, polyethyleneglycol or glycerol, using surfactants, etc.

Tablets (including vaginal tablets) may be prepared in which the powdered mixture is processed to form granules, mixed with other substances if necessary and then further compressed, for example. The tablets may contain various excipients, e.g. starches, lactose, sucrose, glucose, sodium chloride, urea for soluble or injectable tablets, amylose, various types of cellulose as described above, etc. Glycerol or starch may be added, for example, as moisture retaining agents.

The disintegrants used may be, for example, starch, alginic acid, calcium alginate, pectic acid, powdered agar-agar, formaldehyde gelatine, calcium carbonate, calcium phosphate, sodium bicarbonate, magnesium peroxide or amylose.

Agents to counter disintegration or dissolving which may be used include, for example, cane sugar, stearin, solid paraffin (preferably with a melting point in the range from 50–52° C.), cocoa butter and hydrogenated fats.

Suitable resorption accelerators include inter alia quaternary ammonium compounds, sodium laurylsulphate, saponins.

Ether, for example, may be used as a binder distributor while cetylalcohol, glycerol monostearate, starch, lactose, wetting agents (e.g. aerosol OT, Pluronics, Tweens) and others may be used as hydrophilising agents or as breakdown accelerators.

Moreover, the following may be used as tablet excipients in general: Aerosil, silicic acids, silicon dioxide, Aerosol OT ethylcellulose, Amberlite resin, XE-88, Amijel, Amisterol, amylose, Avicel microcrystalline cellulose, bentonite, calcium sulphate, Carbowax 4000 & 6000, carrageenin, castor wax, cellulose, microcristalline cellulose, dextrane, dextrin, pharmaceutical tablet base, kaolin, spray dried lactose (USP), Lactosil, magnesium stearate, mannitol, granular mannitol N. F. methylcellulose, Miglyol 812 neutral oil, powdered milk, lactose, nal-tab, Nepol-Amylose, Pöfizer crystalline sorbitol, Plasdone, polyethyleneglycols, polyvinylpyrrolidone, Precirol, calves' foot oil (hydrogenated), melting tablet base, silicones, Stabiline, Sta-rx 1500, Syloid, Waldhof tablet base, Tablettol, Talcum cetylatum and stearatum, Tego metal soaps, glucose sodium carboxymethyl starch, crospovidone, croscarmellose sodium, hydroxypropylcellulose, hydroxypropyl-methylcellulose, and tylose. The tabletting excipient K (M25) is particularly suitable, which also meets the requirements of the following Pharmacopoeias: DAB, Ph, Eur, BP, JP and NF.

To achieve delayed release, agents such as ethyl cellulose, carboxypolymethylene, hydroxypropylmethylcellulose, carboxymethyl cellulose, methacrylic acid copolymer, cellulose acetate phthalate or polyvinyl acetate may be used.

Other excipients from the prior art may also be used.

The tablets may also consist of several layers. Coated tablets may be prepared accordingly by coating cores produced analogously to the tablets with substances normally used for tablet coatings, for example polyvinylpyrrolidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

The tablets may be prepared for example by direct compression.

Other orally administred formulations may also be prepared, such as suspensions, solutions, emulsions, syrups, elixirs, etc. If desired, the compound may be microencapsulated.

Syrups containing the active substances or combinations thereof according to the invention may additionally contain a sweetener such as saccharine, cyclamate, glycerol or sugar and a flavour enhancer, e.g. a flavouring such as vanilline or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

The compound may be administered parenterally by dissolving, emulsifying or suspending it in a liquid and injecting it by subcutaneous, intramuscular or intravenous route. Suitable solvents include, for example, water or oily media.

Injectable solutions are prepared in the usual way, e.g. with the addition of preservatives such as hydroxybenzoates or stabilisers such as complexones, and transferred into injection vials or ampoules.

To prepare suppositories, the compound may be formulated with low-melting and water-soluble or water-insoluble materials such as polyethyleneglycol, cocoa butter, higher esters (e.g. myristyl palmitate) or mixtures thereof.

EXAMPLES

1. Metabolism

To determine the metabolism the enzyme CYP2D6 was reacted with 2'-Chloro-3',5'-dimethoxyphen-1'-yl-imino-2-imidazolidine. After 30 minutes 2.4% of the substance had been broken down by the enzyme.

2. Efficacy and Selectivity

The efficacy and selectivity of 2'-Chloro-3',5'-dimethoxyphen-1'-yl-imino-2-imidazolidine is determined as follows:

| activity in the dog | activity on human urethra | selectivity in the dog |
|---|---|---|
| 65 | 66.2 | 0.64 |

The maximum contraction in the isolated dog femoral artery and the human urethra are given as percentages of contraction compared with noradrenaline.

Selectivity in the dog is the difference between the percentage contraction on the dog femoral artery at $10^{-5}$ M and the percentage contraction on the dog carotid artery at $10^{-5}$ M, which reveal uroselectivity.

3. a. Preparation of 2'-Chloro-3',5'-dimethoxyphen-1'-yl-imino-2-imidazolidine Free Base Step 1

50 g of 3,5-Dimethoxyaniline were dissolved in 250 ml of toluene. 32.4 ml of acetic anhydride were slowly added. The solution was stirred at r.t. overnight. Petrol ether was then added and the product was filtered, washed and dried.

63.5 g of N-Acetoxy-3,5-dimethoxyaniline were obtained as a solid, m.p. 163–165° C.

Step 2

56.5 g of N-Acetoxy-3,5-dimethoxyaniline were dissolved in 200 ml of acetic acid. The solution was cooled to 0° C. and 150 ml of a 32% hydrogen chloride solution were added. A solution of 12.75 g of sodium chlorate in 15 ml of water were added dropwise. A viscous ochre yellow paste was formed which was further reacted over 0.5 h at 2° C., then filtered, washed with water and dried.

33.0 g of N-Acetoxy-2-chloro-3,5-dimethoxyaniline were obtained as an ochre yellow solid, m.p. 117–118° C.

Step 3

33.0 g of N-Acetoxy-2-chloro-3,5-dimethoxyaniline were dissolved in 2 l of ethanol and refluxed with 400 ml of potassium hydroxide. After 2 h 500 ml water were added and the ethanol was evaporated under reduced pressure. The aqueous phase was then extracted with 2×250 ml of ether. The ethereal phase was dried over magnesium sulfate and concentrated.

28 g of 2-chloro-3,5-dimethoxy-aniline were obtained

Step 4

14.4 g of potassium isocyanate were dissolved at 10° C. in 450 ml of acetone. 14.2 ml of benzoylchloride were added dropwise carefully. The white suspension was refluxed 10 minutes and then cooled again to 10° C. A solution of 28 g of 2-chloro-3,5-dimethoxyaniline in 300 ml of acetone was then added and the obtained mixture refluxed over 3 h. 700 ml of water with ice were added and the aqueous phase was extracted with 3×600 ml of ethyl acetate. The organic phase was then dried over magnesium sulfate and concentrated. The brown residue was dissolved in 100 ml ethanol and refluxed together with 35 ml of an aqueous solution of potassium hydroxide. After 1 hour, 500 ml of water were added. Ethanol was distilled under reduced pressure. The brown solution was neutralized with 300 ml of an ammonium chloride solution and the solid which precipitated was filtered, washed with water and dried.

35 g of (2-chloro-3,5-dimethoxy-phenyl)-thiourea were obtained as a brown powder, m.p. 159–162° C.

Step 5

35 g of (2-chloro-3,5-dimethoxy-phenyl)-thiourea were dissolved in 150 ml of methanol. 6.6 ml of methyl iodide were added dropwise and the mixture was refluxed over 2 h. The solid was then filtered, washed with ether and dissolved again in 110 ml of methanol. 11 ml of ethane-1,2-diamine were added and the mixture refluxed over 8 h. A white powder precipitated which was filtered, washed with methanol, ethyl acetate and ether and dried.

53.3 g of 2'-Chloro-3',5'-dimethoxy-phen-1'-yl-imino-2-imidazolidine were obtained as a white powder, m.p. 204–206° C.

3. b. Preparation of 2'-Chloro-3',5'-dimethoxyphen-1'-yl-imino-2-imidazolidine-hydrochloride 2.2 g of 2'-Chloro-3',5'-dimethoxy-1'-yl-imino-2-imidazolidine free base were suspendend in 10 ml methanol in an ultrasound bath. 10 ml of a 1 M solution of HCl/Ether were added. Then diethylether was added until formation of a white precipitate. The precipitate was filtered off, washed with ether and dried.

2.5 g (95%) 2'-Chloro-3',5'-dimethoxy-1'-yl-imino-2-imidazolidine Hydrochloride were obtained as a white powder; m.p. 203–205° C.

$^1$H NMR (400 MHz, DMSO-d6): d=10.60 (NH), 8.38 (NH), 6.73 (1H, d, J=2.7 Hz, aryl-H), 6.64 (1H, d, J=2.7 Hz, aryl-H), 3.88 (3, s, OCH$_3$), 3.81 (3H, s, OCH$_3$), 3.65 (4H, s, Imidazolidine-CH$_2$). MS m/z 256/258 (100/43) (M+H)$^+$ Other acid addition salts than the hydrochloride can be prepared by procedures well known in the art.

The other compounds described can be prepared likewise, starting from the corresponding 3,5-Dialkoxyaniline in the first step, followed by analogous halogenation as described or other well known halogenation procedures. Steps 3 to 6 follow the procedure as described.

4. Pharmaceutical Composition

Example A

Tablets

| | |
|---|---|
| 2'-Chloro-3',5'-dimethoxyphen-1'-yl-amino-imidazolidine in the form of the hydrochloric acid salt | 1 mg |
| Lactose | 105 mg |
| Microcrystaline celulose | 30 mg |
| Corn starch | 30 mg |
| Povidon | 5 mg |
| Sodium carboxymethyl starch | 5 mg |
| Colloidal silica | 3 mg |
| Magnesium stearate | 1 mg |
| Total | 180 mg |

Preparation: The active substance is mixed with some of the excipients and granulated in the usual way. The granules are sieved, combined with the remaining excipients and compressed into tablets weighing 180 mg.

Example B

Ampouless

| | |
|---|---|
| 2'-Chloro-3',5'-dimethoxyphen-1'-yl-amino-imidazolidine- in the form of the hydrochloric acid salt | 1.0 mg |
| Sodium chloride | 18.0 mg |
| Sufficient water for injection to male up to | 2.0 mL |

Preparation: The active substance and sodium chloride are dissolved in water for injection and transferred into glass ampoules in an aseptic condition.

Example C

Capsules

| | |
|---|---:|
| 2'-Chloro-3',5'-dimethoxyphen-1'-yl-amino-imidazolidine in the form of the hydrochloric acid salt | 1 mg |
| Lactose | 178 mg |
| Magnesium stearate | 1 mg |
| Total | 180 mg |

Preparation: The active substance is mixed with the excipients and filled into capsules in the usual way.

What is claimed is:

1. A compound according to formulas I or II

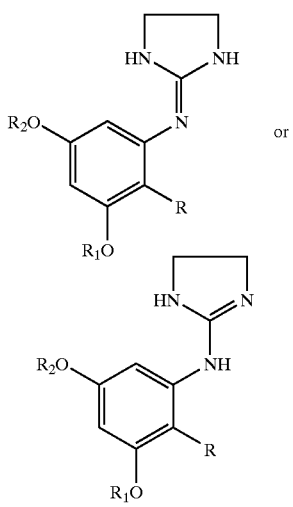

wherein

R is F, Cl, Br, $CF_3$, $CH_2F$ or $CHF_2$ and $R_1$ and $R_2$ independently of each other are $C_1$ to $C_6$-alkyl; or a pharmacologically acceptable salt of any of the two tautomeres.

2. The compound according to claim 1 wherein R is F, Cl, Br or $CF_3$ and $R_1$ and $R_2$ independently of each are an unbranched $C_1$ to $C_6$-alkyl.

3. The compound according to claim 1 wherein R is Cl, Br or $CF_3$ and $R_1$ and $R_2$ both being the same unbranched $C_1$ to $C_4$-alkyl.

4. The compound according to claim 1 wherein R is Cl or Br and $R_1$ and $R_2$ both are methyl, ethyl or propyl.

5. The compound according to claim 1 wherein R is Cl and $R_1$ and $R_2$ both are methyl or ethyl.

6. A compound chosen from

2'-chloro-3',5'-dimethoxyphen-1'-yl-imino-2-imidazolidine,

2'-chloro-3',5'-diethoxyphen-1'-yl-imino-2-imidazolidine,

2'-chloro-3',5'-dipropyloxyphen-1'-yl-imino-2-Imidazolidine,

2'-bromo-3',5'-dimethoxyphen-1'-yl-imino-2-imidazolidine,

2'-bromo-3',5'-diethoxyphen-1'-yl-imino-2-imidazolidine and

2'-bromo-3',5'-dipropyloxyphen-1'-yl-imino-2-imidazolidine or a tautomeric thereof and/or a pharmacologically acceptable salt thereof.

7. A compound chosen from:

2'-Chloro-3',5'-dimethoxyphen-1'-yl-imino-2-imidazolidine represented by the formula:

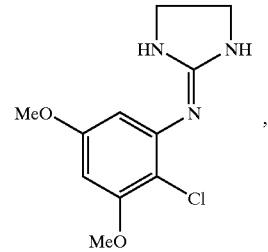

and its tautomeric 2'-chloro-3',5'-dimethoxyanilino-2-imidazoline represented by the formula:

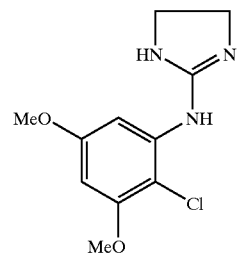

or a pharmacologically acceptable salt of any of the two tautomeres.

8. The compound according to claim 7, wherein the pharmacologically acceptable salt is the hydrochloride.

9. A method of treating urinary incontinence comprising administering to a patient in need thereof a pharmaceutically effective amount of a compound according to claim 1.

10. The method according to claim 9 wherein the administration is oral.

11. A pharmaceutical composition comprising a pharmaceutically effective amount of a compound according to claim 1.

12. The pharmaceutical composition according to claim 11 wherein the pharmaceutically effective amount is between 0.001 mg and 1 g.

13. The pharmaceutical composition according to claim 11 wherein the pharmaceutically effective amount is between 0.001 mg and 100 mg.

14. The pharmaceutical composition according to claim 11 wherein the pharmaceutically effective amount is between 0.01 mg and 10 mg.

15. The pharmaceutical composition according to claim 11 in the form of a tablet, or a capsule.

16. A pharmaceutical composition comprising a pharmaceutically effective amount a compound according to claim 7.

17. A method of treating urinary incontinence comprising orally administering to a patient in need thereof a pharmaceutically effective amount of a composition according to claim 16.

18. The method according to claim 17 wherein the pharmaceutically effective amount is between 0.001 mg and 1 g.

19. The method according to claim 17 wherein the pharmaceutically effective amount is between 0.001 mg and 100 mg.

20. The method according to claim 17 wherein the pharmaceutically effective amount is between 0.01 mg and 10 mg.

* * * * *